United States Patent [19]

Anderson

[11] Patent Number: 4,968,027
[45] Date of Patent: Nov. 6, 1990

[54] WEIGHT LIFTERS BELT WITH THERAPEUTIC LUMBAR REGION

[76] Inventor: Kip Westley Anderson, 6450 Abington, Detroit, Mich. 48228

[21] Appl. No.: 396,321

[22] Filed: Aug. 21, 1989

[51] Int. Cl.⁵ ............................................ A63B 21/072
[52] U.S. Cl. ...................................... 272/123; 2/322; 2/338; 128/78
[58] Field of Search .................... 272/123; 128/33, 78, 128/594; 2/321, 322, 338, 339

[56] References Cited

U.S. PATENT DOCUMENTS

| | | | |
|---|---|---|---|
| 4,217,705 | 8/1980 | Donzis | 128/594 X |
| 4,267,611 | 5/1981 | Agulnick | 128/33 X |
| 4,552,135 | 11/1985 | Racz et al. | 128/78 |
| 4,689,833 | 9/1987 | Daniels | 128/78 X |
| 4,744,351 | 5/1988 | Grundei et al. | 128/78 |
| 4,745,911 | 5/1988 | Bender | 128/78 |
| 4,756,306 | 7/1988 | Curlee | 128/78 |
| 4,768,499 | 9/1988 | Kemp | 128/78 |

OTHER PUBLICATIONS

Hawley's Condensed Chemical Dictionary, pp. 224-225 and 315, 1987.

*Primary Examiner*—Robert W. Bahr
*Attorney, Agent, or Firm*—Harness, Dickey & Pierce

[57] ABSTRACT

A weight lifting belt including a midsection of increased width and a therapeutic lumbar region central disposed on the interior surface of the midsection. The therapeutic lumbar region consists of a moldable mass for occupying the spinal column depression in the lumbar region of a weight lifter and a leather covering attaches the moldable mass to the midsection of the belt. When properly positioned on a weight lifter, the moldable mass fills and conforms to the shape of the spinal column depression of the weight lifter enabling the weight lifting belt to provide constant support and uniform pressure to the muscles of the lumbar region.

5 Claims, 1 Drawing Sheet

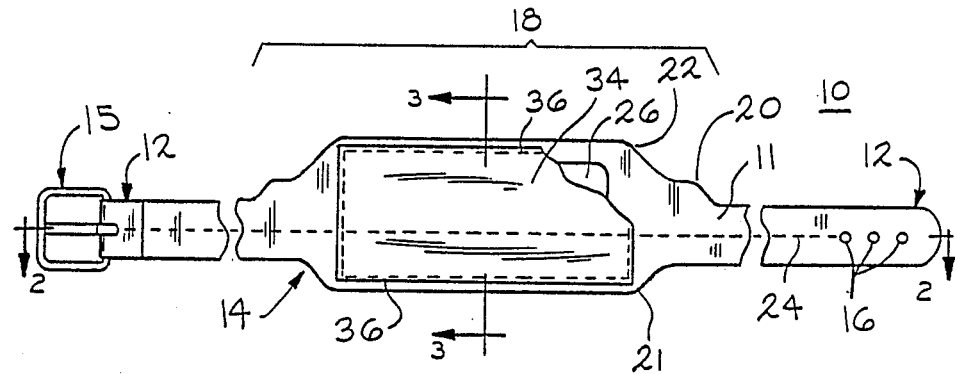
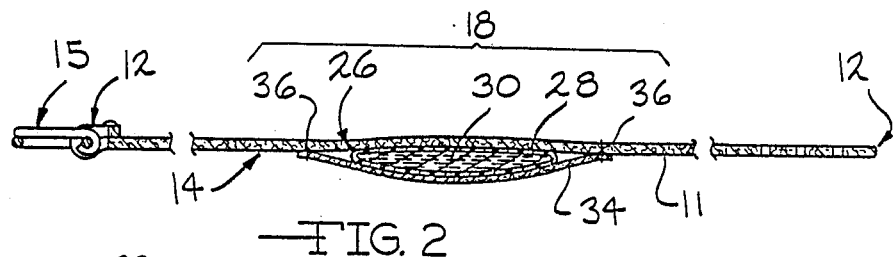
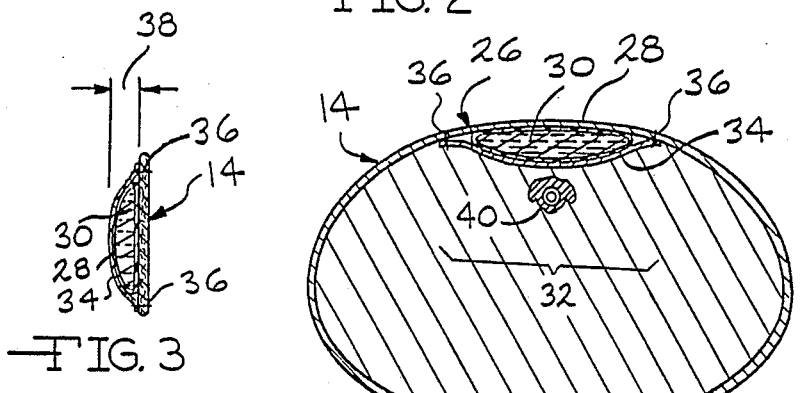
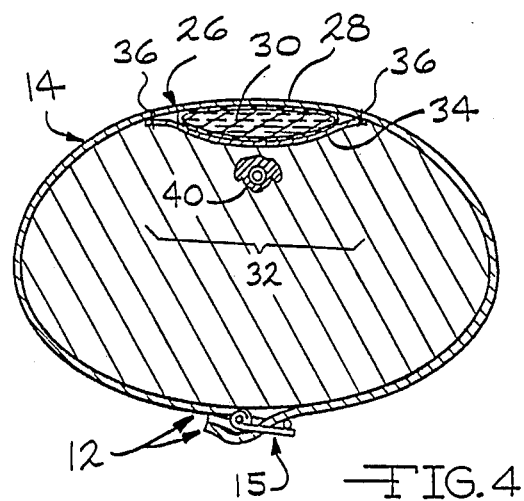

WEIGHT LIFTERS BELT WITH THERAPEUTIC LUMBAR REGION

BACKGROUND OF THE INVENTION

The invention relates to a weight lifting belt with a therapeutic lumbar region centrally located where the belt crosses the weight lifter's lower back. More particularly, the invention relates to a leather weight lifting belt constructed with a packet of water in a gelatinous state (hereinafter the gel pack) disposed between the leather strap or primary support wall of the weight lifting belt and a leather covering. Thus, the gel pack is completely enclosed in the belt. The leather covering is attached to the primary support wall of the weight lifting belt as a protective covering for the gel pack. In addition, the leather covering increases the strength, durability and visual enhancement of the overall product. The gel pack is located on the primary support wall of the weight lifting belt so as to be positioned centrally across the lower back, also known as the lumbar region, of the weight lifter. So positioned, the invention provides constant support and uniform pressure to the lumbar region.

In today's society of heightened health consciousness, physical fitness has become of increased importance. Many forms of physical fitness have experienced recent gains in popularity. This is also true of weight lifting. While weight lifting is an excellent form of physical exercise, it can also prove to be a dangerous form. Danger in the weight room comes not only from mechanical devices and the heavy amount of weight attached to each device, but also from improper technique and over exertion (lifting excessive weight) on the part of a weight lifter during an exercise. The results of these self-inflicted dangers are often sore, strained and torn muscles.

Nowhere is this danger more prevalent than in the weight lifter's lumbar region. The lumbar region being generally described as that part of the back and sides of the body located between the lowest ribs and the hips. The muscles of the lumbar region can be easily strained or torn during over exertion A same result can occur when improper technique is employed while exercising the muscles of not only the lumbar region, but also those of the leg and chest regions of the body.

In order to combat the dangers to the lumbar region muscles, weight lifters employ what is generally known as the weight lifting belt. Typically, a weight lifting belt is constructed out of a heavy leather strap with a common fastener attached to each end. A belt buckle and a series of belt holes are most regularly employed as the common fastener. However, strips of the hook and loop fastener "Velcro" are also routinely used.

Proceeding transversely across the length of a typical weight lifting belt, the belt begins to widen upon reaching the beginning of the weight lifter's lumbar region, both upwardly and downwardly from the belt's centerline. In some styles of weight lifting belts, the downward increase in width will mirror the upward increase in width. In other styles, the increases in width will occur at different points transversely along the belt's centerline. Another style of weight lifting belts provide "extra" support for the lumbar region muscles. These belts tend to exhibit an upward increase in width, from the belt's centerline, that is greater than the corresponding downward increase in width.

Upon reaching the midpoint of the lumbar region, more easily recognized as the weight lifter's spinal column, weight lifting belts tend to mirror themselves along a vertical axis corresponding to the spinal column until passing completely across the lumbar region. Once across the weight lifter's lumbar region, the weight lifting belt continues at a width equal to that of the previous end, until reaching the opposing common fastener.

The purpose of the extra width across the lumbar region of a weight lifting belt is two fold. The first is to assist the weight lifter in maintaining proper technique during exercises where muscles, other than those in the lumbar region, are being used or isolated. The proper technique encouraged by the weight lifting belt is that of a straight back. A straight back prohibits the weight lifter from excessively using the muscles of the lumbar region to assist those muscles being isolated during the exercise.

When improper technique is employed during a lift, a situation more likely to occur without a weight lifting belt, the possibility of excessive strain being applied to the muscles of the lumbar region increases. In actual practice, the amount of excessive strain possibly being applied to the lumbar region muscles varies from exercise to exercise.

A second purpose of the extra width in a weight lifting belt is to provide extra support for the lumbar region muscles and other relatively weak areas of the body during a lift. These weak areas include the kidney, abdominal and other weak areas of the body. Support is provided in the form of pressure applied to the weight lifter's lumbar region. The pressure is induced by tightening the weight lifting belt. This increased pressure enables the weight lifter to reduce the amount of work that must be performed by the muscles of the lumbar region during that lift.

While the typical weight lifting belts do help prevent injury to the lumbar region muscles by encouraging proper technique and providing support, they have limitations. After a relatively short period of time, depending upon the frequency and duration of use, a weight lifting belt will begin to show evidence of wear. While not rendered unusable, the belt does lose some of its effectiveness.

One problem of wear occurs across the wide lumbar area of the weight lifting belt. In particular, the leather along the centerline of the weight lifting belt begins to breakdown in strength. This breakdown is caused in part by a stretching of the leather along the belt's centerline. Stress concentrations, induced by the widening of the weight lifting belt in the lumbar region, tend to localize the stretching to the belt's centerline. With this breakdown, the belt will exhibit a bow toward the user. A weight lifting belt exhibiting this inward bow is effectively reduced in its ability to encourage the use of a straight back technique. Again, the possibility of injury arises.

Another generally occurring problem in weight lifting belts is the inability of the belt to provide uniform back support to the user. It is known that the lumbar region is not uniformly shaped from one person to another, nor from the left side of the body to the right. While some individuals may exhibit a rounded lumbar region, most will exhibit a depression in the area of their spinal column. The typical lifting belt fails to account for these differences.

Common weight lifting belts remain in contact with the entire lumbar region of very few weight lifters. The problem becomes aggravated as the muscles along the sides of the spinal column grow and increase in size. Therefore, in most instances, the belt will only make contact with the left and right sides of the user's lumbar region forming a bridge-like span across the depression of the spinal column region.

The weight lifting belt of the present invention is especially adapted to remain in contact with the weight lifter's body across the entire lumbar region for all possible user variations. This is achieved by attaching the gel pack to the weight lifting belt so that the gel pack will be centrally presented to the lumbar region of the user. In so doing, the present invention provides constant support and uniform pressure across the user's entire lumbar region.

The present invention also overcomes various other disadvantages of the prior art weight lifting belts. Particularly, the invention eliminates the tendency of a worn weight lifting belt to bow inwardly. This is achieved by staggering the increases in width in combination with the gel pack filling the depression of the spinal region. The result of these improvements is a weight lifting belt that encourages proper technique, provides uniformly distributed pressure and support, increases user comfort, reduces the threat of injury, and thus promotes greater physical fitness.

SUMMARY OF THE INVENTION

This invention relates to a weight lifting belt with a centrally located therapeutic lumbar region. In particular, the invention relates to an improved leather weight lifting belt constructed with a packet of water, in a gelatinous state, centrally disposed in the lumbar region of the weight lifting belt between the primary support wall and a leather covering. The leather covering is stitched along its perimeter to the primary support wall and wholly encloses the gel pack in the belt. The gel pack is located along the primary support wall so as to be positioned centrally across the lumbar region of a weight lifter wearing the belt.

The weight lifting belt of the present invention is designed to correct the problems and limitations associated with weight lifting belts. In particular, these include the general inability of a weight lifting belt to provide constant support and uniform pressure to the entire lumbar region of the user and the failure of a worn belt to encourage the employment of proper technique by a user.

One aspect of the present invention is that the improved weight lifting belt is adapted to remain in contact with the user's body across the entire lumbar region. This is accomplished with the addition of the gel pack.

The gel pack itself includes a rectangular plastic container enclosing a gelatinous suspension. The gelatinous suspension is created by the addition of a viscosity increasing agent to water. Several types of viscosity increasing agents may be used, including cornstarch or methylcellulose.

The gel pack is positioned on the primary support wall of the weight lifting belt so as to be centrally located over the spinal depression in the lumbar region of the user. Containing a viscous fluid, the gel pack fills and conforms to the shape of the weight lifter's spinal depression while the belt is being worn. As the belt is tightened around the user, the gel pack is compressed and becomes firm. This occurs because of the containment of the gelatinous suspension within the packet. Support and pressure is then uniformly applied across the weight lifter's entire lumbar region from the weight lifting belt.

The gel pack is held in position by a leather covering. The cover is placed over the gel pack so that no portion of the gel pack is exposed. Once so positioned, the cover is attached to the primary support wall of the belt by stitching along its perimeter. The covering serves several functions including protection of the gel pack and increasing the strength, durability and visual enhancement of the overall product.

So positioning the gel pack enables the present invention to overcome the other limitations of prior art weight lifting belts. Specifically, the weight lifting belt is no longer able to assume the inward bow exhibited by "worn out" or "well used" belts. Once occupying the spinal depression, any compression on the gel pack is firmly resisted due to the compartmental restrictions on the fluid's flow. Also, the sewing of the leather cover to the primary support wall of the belt adds reinforcement to the primary support wall and thus inhibits any stretching along the belt's centerline.

Additional benefits and advantages of the present invention will become apparent to those skilled in the art to which this invention relates from the subsequent description of the preferred embodiments and the appended claims, taken in conjunction with the accompanying drawings.

BRIEF DESCRIPTION OF THE DRAWINGS

FIG. 1 is an elevational view of the weight lifting belt of the present invention partially cut away to show the gel pack;

FIG. 2 is a cross sectional view along lines 2—2 in FIG. 1 of the weight lifting belt of the present invention;

FIG. 3 is a cross sectional view along lines 3—3 in FIG. 1 of the weight lifting belt of the present invention; and FIG. 4 is a cross sectional view, similar to that of FIG. 2, wherein the weight lifting belt of the present invention is circumferentially engaged around the torso of a weight lifter.

DETAILED DESCRIPTION OF THE DRAWINGS

With reference to the drawings, a weight lifting belt 10 (hereinafter belt 10), constructed according to the principles of the present invention, is shown in FIG. 1 when viewed toward an interior surface 11 of the belt 10. At each end 12 of a leather strap 14 of the belt 10, a common fastening means is attached. The strap 14 is the primary support wall of the belt 10. The embodiment shown in FIG. 1 depicts a belt buckle 15 and a series of belt holes 16 at ends 12 of the belt 10 as the common fastening means. Other means, including a hook and loop fastener may also be employed.

Proceeding lengthwise from the end 12 with the belt holes 16, the strap 14 begins to widen upon reaching a midsection 18 portion of the belt 10. The midsection 18 corresponds with the lumbar region of a weight lifter.

Once at the midsection 18, the strap 14 exhibits alternating increases in width from an imaginary centerline 24 of strap 14. The first increase in width is an upward increase 20 from the centerline 24. The second increase in width is a downward increase 21 from the centerline 24. The last increase in width is another upward increase 22 from the centerline 24. The total upward increase in width is approximately twice that of the downward increase in width.

Positioned centrally to the length and width of the midsection 18 of the strap 14 is a gel pack 26. The gel pack 26 is positioned on the midsection 18 of the belt 10 so as to fill and conform to a spinal depression 32 in the lumbar region of a weight lifter (see FIG. 4). The gel pack 26 is constructed of a thin plastic sheeting thermally sealed along its edges to form a generally pillow shaped container 28, as shown in FIG. 2.

Disposed in container 28 is gelatinous composition 30 of water and a viscosity increasing agent. The viscosity increasing agent in the present invention is cornstarch. However, other viscosity increasing agents may be used, including methylcellulose.

The gel pack 26 is securely held to the interior surface 11 of the strap 14 by a leather covering 34. The dimensions of the leather covering 34 are slightly larger than, but conforming to, those of the gel pack 26. Stitching 36 along the perimeter of the cover 34 attaches the cover 34 to the interior surface 11 of the strap 14. Once the gel pack 26 and cover 34 are positioned and attached to the strap 14, they form a generally inward (toward the weight lifter) bulge 38, as best shown in FIGS. 2, 3, and 4.

When the belt 10 is properly positioned around the waist of the weight lifter, as seen in FIG. 4, the bulge 38 created by the gel pack 26 and cover 34 tends to fill and conform to the shape of the spinal depression 32 in the lumbar region of the weight lifter. The center of the spinal depression 32 and the bulge 38 will generally correspond with the weight lifter's spinal cord 40. This center will also generally correspond to the halfway mark of the midsection 18 of the belt 10 (lines 3—3 in FIG. 1).

Upon reaching the halfway mark of the midsection 18, the belt 10 tends to mirror itself along lines 3—3 in FIG. 1 and alternatingly decrease in width as the strap 14 reaches the end of the midsection 18. The belt 10 then proceeds toward opposite end 12 and the belt buckle 15.

It is to be understood that the invention is not limited to the exact construction or method illustrated and described above, but that various changes and modifications may be made without departing from the spirit and scope of the invention as defined in the following claims.

What is claimed is:

1. A weight lifting belt comprising:
   a strap including a midsection non-symetrically increasing in width in an upward and downward direction, said strap also including a means for fastening said belt around the waist of a person; and
   a therapeutic lumbar region disposed centrally on said midsection of said strap, said therapeutic lumbar region including a movable thin-walled container enclosing a fixed volume of moldable mass for occupying the spinal column depression of said person, said fixed volume of moldable mass being a gelatinous state of water produced by the addition of a viscosity increasing agent to said water, said thin-walled plastic container being wholly enclosed and retained in said lumbar region by a durable covering of thin pliable material being separately fastened to said strap, said container being thin walled relative to said covering material and said covering material being thin relative to said strap whereby said strap causes said moldable mass to readily deform inducing said container and covering material to substantially conform to the lumbar region of a person in response to said belt being fastened around the waist of that person.

2. A weight lifting belt as set forth in claim 1 wherein said fastening means comprises a belt buckle and a series of belt holes.

3. A weight lifting belt as set forth in claim 1 wherein said fastening means comprises a hook and loop fastener.

4. A weight lifting belt as set forth in claim 1 wherein said viscosity increasing agent is cornstarch.

5. A weight lifting belt as set forth in claim 1 wherein said viscosity increasing agent is methylcellulose.

* * * * *